(12) United States Patent
Bendahan et al.

(10) Patent No.: US 7,233,644 B1
(45) Date of Patent: Jun. 19, 2007

(54) COMPUTED TOMOGRAPHIC SCANNER USING RASTERED X-RAY TUBES

(75) Inventors: Joseph Bendahan, San Jose, CA (US); Walter I Garms, Palo Alto, CA (US)

(73) Assignee: GE Homeland Protection, Inc., Newark, CA (US)

( * ) Notice: Subject to any disclaimer, the term of this patent is extended or adjusted under 35 U.S.C. 154(b) by 0 days.

(21) Appl. No.: 11/001,256

(22) Filed: Nov. 30, 2004

(51) Int. Cl.
*G01N 23/04* (2006.01)
(52) U.S. Cl. ............................................. 378/57; 378/9
(58) Field of Classification Search ............... 378/4, 378/9, 10, 19, 57
See application file for complete search history.

(56) References Cited

U.S. PATENT DOCUMENTS

| | | | |
|---|---|---|---|
| 4,045,672 A | 8/1977 | Watanabe | 378/10 |
| 5,712,889 A | 1/1998 | Lanzara et al. | 378/19 |
| 5,966,422 A * | 10/1999 | Dafni et al. | 378/9 |
| 6,735,271 B1 | 5/2004 | Rand et al. | 378/4 |
| 2004/0017888 A1 * | 1/2004 | Seppi et al. | 378/57 |

OTHER PUBLICATIONS

Hori, Keiichi et al., "Development of Ultra-Fast-X-ray Computed Tomography Scanner System," Reprinted from 1997 Nuclear Science Symposium, Nov. 9-15, 1997, pp. 1003-1008.
Yue, G.Z. et al., "Generation of continuous and pulsed diagnostic imaging x-ray radiation using a carbon-nanotube-based field-emission cathode," *Applied Physics Letters*, vol. 81, No. 2, Jul. 8, 2002, pp. 355-357.

* cited by examiner

*Primary Examiner*—Courtney Thomas
(74) *Attorney, Agent, or Firm*—Eugene Hyun, Esq.; Armstrong Teasdale LLP

(57) ABSTRACT

A high speed computed tomography x-ray scanner using a plurality of x-ray generators. Each x-ray generator is scanned along a source path that is a segment of the scanner's source path such that each point in the source path is scanned by at least one tube. X-ray generators and detectors can be arranged in different scan planes depending on the available hardware so that a complete and near planar scan of a moving object can be assembled and reconstructed into an image of the object.

46 Claims, 16 Drawing Sheets

COMPUTED TOMOGRAPHIC SCANNER USING RASTERED X-RAY TUBES

BACKGROUND OF THE INVENTION

1. Field of the Invention

This invention relates generally to computed tomographic (CT) scanners and, more particularly, to CT scanners that use electron rastered x-ray generators or other means of projecting an electron beam to different positions on the anode.

2. Description of the Related Art

For many applications, CT is currently a preferred method for scanning objects using x-rays. CT allows a two- or three-dimensional image of the interior of an object to be constructed without physical intrusion into the object. For example, CT can be used to develop a three-dimensional image of the contents of baggage without physically opening the baggage, as would be useful in airport security screening. CT scanners are also used for medical applications (for example to scan different parts of the body), in industrial applications (for example in rapid prototyping and reverse engineering), and for non-destructive testing (for example to detect defects of turbine blades and ceramics).

The fundamental principles of CT are well known. In one approach, a fan of x-rays is projected from a source point through the object onto a detector array. Each beam within the fan propagates through the object along a different trajectory in a scan plane and the detector element that collects that beam therefore collects information about the object along the trajectory. The information collected from propagation of the x-ray fan shall be referred to as a view. This process is repeated for many different source points (the locus of source points shall be referred to as the source path), generating multiple views of the object. The views are then combined using various reconstruction techniques, such as filtered back projection, to produce a two-dimensional image of the object. Most reconstruction algorithms require that each point to be reconstructed be traversed by x-rays propagating along all different angles. Rays 180 degrees apart are redundant, so in practice a set of x-rays spanning 180 degrees (rather than a full 360 degrees) is sufficient. The set of views that together provide rays of 180 degrees for each point is referred to as a full set of views. The source path of the scanner preferably is sufficient to provide a full set of views (either directly or through interpolation or other techniques).

The basic process for producing two-dimensional images can be extended to produce a three-dimensional image of the object. In a common approach, a full set of views is acquired at different "depths" along the object, each full set of views is used to produce a two-dimensional slice of the object at the corresponding depth, and the slices are then pieced together to form a three-dimensional image. This slice-based approach is generally preferred for industrial CT systems. In another common approach, views are acquired as the object is continuously translated relative to the CT scanner. As a result, rather than acquiring a full set of views at a fixed depth coordinate (as is the case in the slice-based approach), each view is acquired at a slightly different depth coordinate due to the object translation and interpolation can be used to fill in gaps as necessary. This method is often referred to as spiral or helical scanning and is generally preferred for medical applications. Regardless of whether slice or spiral scanning is used, the resulting three-dimensional images can be displayed using a wide range of conventional graphics techniques.

One drawback to conventional CT systems is their slow scanning speed for some applications. The number of views required for a full set and the number of full sets required per object depend on the desired resolution. For even moderate applications, a large number of views may be required to generate satisfactory images of an object. As a result, if views cannot be generated quickly enough, the time required to scan an object will be unacceptably long.

In a common conventional approach, a single x-ray source is used to project an x-ray fan from a source point to a detector array. The x-ray source and the detector array are mounted on a gantry on opposite sides of the object. The entire gantry is mechanically rotated about the object to generate the required views. At a typical rotation speed of two revolutions per second, several seconds may be required to scan a single object. If the objects are luggage being screened, for example, this typically results in a throughput of less than 500 bags per hour.

The inspection time can be reduced in a number of ways. In one conventional approach, the gantry is rotated at a higher frequency. However, the gantry can be large and rotating it at high speeds can introduce its own problems, not the least of which is the increased centrifugal force exerted on the gantry. The rotational frequency can be reduced by acquiring several views simultaneously using multiple detector arrays (e.g., multi-slice detectors). However, this requires multiplying the number of detectors that are used. For example, acquiring two views simultaneously typically requires twice as many detectors. This adds cost and complexity to the system.

U.S. Pat. No. 4,352,021 (Boyd, et al.) suggests another approach for generating views. This approach uses a stationary, semi-circular x-ray target that encompasses the object. An electron beam is scanned across the entire x-ray target. One scan of the electron beam across the entire x-ray target traverses the entire source path and generates a full set of views. The electron beam scanning is faster than mechanical rotation of a gantry so higher throughput can be achieved. However, the semi-circular x-ray target may be several feet in diameter for many common applications. As a result, a large electron beam assembly, accurate devices for deflecting the electron beam, and long propagation paths for the electron beam are typically required. This assembly also makes it difficult to scan objects on a conveyor belt because the tube assembly occupies a large volume on one end of the scanner. The long propagation paths also result in a large overall size for the equipment and increased sensitivity to electromagnetic noise, making it inappropriate for use in industrial environments such as airports. The large assembly, which must be kept under vacuum, is also difficult to make leak proof. In order to maintain vacuum, a vacuum pump system is required. The high scanning speed requires a very high tube power in order to achieve a useful x-ray flux.

The Boyd design also has the drawback that the arc of the x-ray source overlaps the arc of the detectors (i.e., source arc+detector arc is greater than 360 degrees), which means that the detector arc and source arc must be displaced in the depth direction. The angle from source to detector with respect to the plane defined by the source arc is referred to as the cone angle. The cone angle, if uncorrected, leads to inaccurate image reconstruction. U.S. Pat. No. 6,735,271 (Rand, et al.) teaches improvements of the Boyd machine by using an x-ray target and detector that are segments of a helix instead of segments of circles. The detector array and target arc are arranged such that active portions of the source and detector are diametrically opposed to each other. This design also provides multislice scanning of an object that is in constant motion at a critical velocity without having to interpolate spiral data.

In another suggested approach, a number of conventional x-ray tubes are positioned around the object and are then turned on and off in sequence. Turning on one x-ray tube activates one source point, generating one x-ray fan and one view of the object. Turning on the next x-ray tube would generate the next view, and so on. However, for many applications, conventional x-ray tubes cannot be spaced close enough to one another to meet the application's resolution requirements.

Some researchers are conducting research into small x-ray generators (nano-tubes). If these devices can be made sufficiently small, then a large number of them can be positioned around the object with an adequate spacing to obtain a high spatial resolution. However, this technology does not appear to be advanced enough for commercial application at this time at voltages greater than 60 kV, which makes this approach inappropriate for medical, baggage scanning and many industrial applications that may require significantly greater x-ray energies. This approach also requires complex systems to distribute power and cooling to the large number of x-ray tubes.

Thus, there is a need for CT scanners that are fast, can provide good spatial resolution, have the capability to scan a large aperture, are cost effective, and/or are able to withstand industrial environments with a compact footprint.

SUMMARY OF THE INVENTION

The present invention overcomes the limitations of the prior art by using a plurality of x-ray generators (e.g., x-ray tubes), preferably located in fixed positions in one or more scan planes, each of which implements a portion of the overall source path. Each x-ray tube is capable of producing x-ray fans projected from different points along the source path. The paths of the x-ray tubes together cover the source path required for a CT reconstruction.

In one approach, the full set of views is generated by rastering the x-ray beams and by activating the x-ray generators in sequence to mimic physical rotation of the source point around the object. In one design, the CT system also includes a plurality of detectors located opposite to the x-ray source, preferably in an arc. The detectors can be arranged in multiple rows to allow for the simultaneous acquisition of multiple slices and can be energy sensitive. In a different design, the x-ray tubes and detectors each form a section of a helix, such that the detector elements are at the same depth as the x-ray target from which they receive x-rays.

In another aspect of the invention, the x-ray tubes are grouped into two or more subscan assemblies that define scan planes that are offset with respect to each other along a depth direction. In some cases, a mechanism (for example, a conveyor belt) moves the object relative to the subscan assemblies along the depth direction. A controller synchronizes activation of the source points to the relative motion of the object, so that continuous slices over the object can be assembled. In one particular geometry, the x-ray tubes are positioned preferably approximating a circular arc about the object and are alternately located on two or more subscan assemblies.

In another aspect of the invention, the x-ray tube includes a source, a raster mechanism and a target. The source generates an electron beam that is directed towards the target. The raster mechanism rasters the electron beam to different locations on the target, thus defining the raster path of the x-ray tube. The x-ray tube may also have a grid for turning the electron beam on and off. By utilizing a plurality of smaller scanning tubes, it is possible to make the tubes sealed, eliminating the need for vacuum pumps on the scanner.

In one particular design, a CT scanner includes two or more subscan assemblies that are offset with respect to each other along a depth direction. Each assembly includes one or more x-ray generators that are stationary with respect to the corresponding scan plane and positioned preferentially approximately in a circular arc about the object. Each x-ray tube is capable of producing x-ray fans projected from source points located on the x-ray tube's raster path. A full set of views is acquired by activating different x-ray tubes in sequence and rastering the source point along the x-ray tubes' raster paths. A mechanism moves the object relative to the subscan assemblies along the depth direction. A controller synchronizes activation of the source points with motion of the object in order to compensate for the offset of the two subscan assemblies.

In another embodiment, a controller records the depth of the object (or position of the transport mechanism) along with the scan data for each view. These views can then be sorted and combined later by computer into data sets appropriate for reconstruction.

In another embodiment, the scanner utilizes two or more subscan assemblies, each with its own set of detectors. The scan assemblies are offset in the depth direction allowing scanning of all the assemblies simultaneously. Simultaneous scanning of multiple planes provides several advantages. The x-ray flux increases proportionally to the number of tubes scanning simultaneously. The scanning speed increases because the time required to traverse the entire source path is divided by the number of assemblies. Alternatively, the x-ray power required for each tube can be reduced while maintaining the same flux and scan speed, reducing the cooling required for the anodes.

These types of CT scanners can be used in many different applications. One application is the inspection of passenger baggage in mass transportation such as airports and break-bulk cargo in air cargo facilities. A system of this design could achieve throughput in excess of 1000 items per hour which is significantly higher than existing rotating gantry designs.

Other aspects of the invention include methods, components and applications of the CT scanners and rastered x-ray tubes described above.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENTS

Figure 1A:
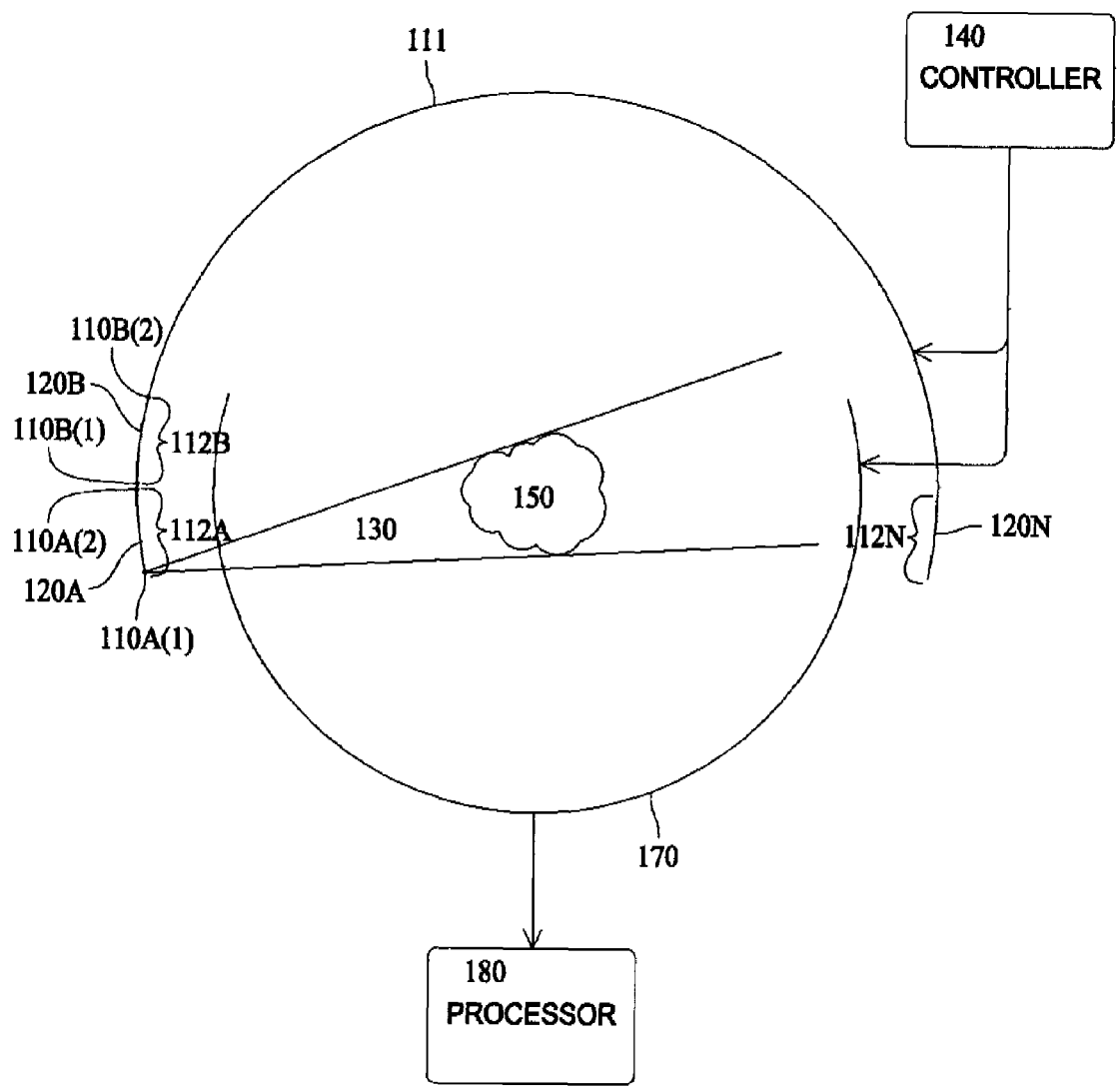
FIGS. 1A–1D are simplified schematic diagrams illustrating CT scanners according to the present invention.

FIGS. 1A–1D are simplified schematic diagrams illustrating CT scanners according to the present invention. In these diagrams, the CT scanner is designed to scan object 150. In many applications, the CT scanner is designed to scan a certain volume or cross-sectional area 150 and objects to be scanned are placed in or moved through the target area 150. For purposes of this application, the terms object and target area or target volume will be used interchangeably. The line 111 represents the source path for the CT scanner and points along the source path shall be referred to as source points. X-ray fans 130 are projected from source points through the object 150 to the detector array 170.

Generally speaking, the CT scanner is designed so that each point in the object 150 is interrogated by x-ray beams propagating at different angles (typically rays spanning 180 degrees are sufficient). A controller 140 controls the source path 111 and/or detector array 170. For example, the controller 140 may activate the source points along the source path 111 according to some sequence (e.g., clockwise around source path 111 in FIG. 1) and may synchronize the detector array 170 to the activation of the source path. Signals from the detector array 170 are transmitted to a processor 180 (intermediate devices are omitted for clarity), and the processor reconstructs images of object 150 from the generated views.

In FIG. 1, a full set of views is generated by activation of all source points along the source path 111. For slice-based CT scanners, a single full set of views can be combined to produce the corresponding slice of the object. For spiral scan CT scanners, two or more full sets may be required to produce a two-dimensional image (due to interpolation requirements, for example), but each full set typically will also be used for more than one two-dimensional image. On average, there will be approximately one two-dimensional image for each full set acquired, even though any particular full set may not alone lead directly to any particular two-dimensional image.

For simplicity, no depth is shown in FIGS. 1A–1D. The source path 111, object 150 and detector array 170 are shown in a single plane. This plane is referred to as the scan plane. The orthogonal direction (in and out of the paper in FIGS. 1A–1D) will be referred to as the depth direction. The situation shown in FIGS. 1A–1D is simplified and is not meant to limit the invention. It should be understood that in many implementations, the source path 111, object 150 and detector array 170 may not be exactly co-planar for all views. The scan plane may have some depth to it, for example if the source path 111 and detector array 170 are not perfectly coplanar. As another example, the object 150 may be moving in the depth direction as the source points are activated in sequence, resulting in a spiral scan over time. Terms such as slice, scan plane, and contiguous source points are meant to include the case of spiral scanning and other similar cases.

In FIGS. 1A–1D, at least some of the x-ray fans 130 are generated by rastered x-ray tubes. In a conventional x-ray tube, an electron beam is accelerated towards a target and impact of the electron beam on the target generates x-rays. However, there typically is only a single point of impact, so the x-rays always emanate from the same location. In a rastered x-ray tube, the x-rays may emanate from different locations. For example, the point of impact may be rastered to different points on a target. The locus of different locations (or at least the points which are on the source path) will be referred to as the raster path for the rastered x-ray tube. In the figures, the raster paths are marked as 120A–120N and will also be used to generally represent the x-ray tubes. The x-ray tubes themselves are omitted in FIGS. 1A–1D for purposes of clarity.

In the example of FIG. 1A, the rastered x-ray tubes and corresponding raster paths 120 are stationary with respect to the scan plane, as is the detector array. The source path 111 is divided into different pieces 112A–112N, each of which is generated by a single rastered x-ray tube. In other words, all of the source points in each of the groups 112 are located on the raster path 120 of a single x-ray tube and the corresponding x-ray fans 130 are generated by scanning the x-ray tube along the raster path 120.

For example, in one approach, the source points are activated in clockwise sequence around the circular arc. The controller 140 first activates the x-ray tube for raster path 120A and the x-ray tube sweeps from source point 110A(1) to source point 110A(2). The controller 140 then activates the x-ray tube for raster path 120B and causes the x-ray tube to scan from source point 10B(1) to 10B(2). This is repeated around the circular arc to the last x-ray tube and raster path 112N. In this way, all views for a slice can be generated without moving the x-ray tubes. Rather, activation of the source points is achieved by scanning the raster paths of the x-ray tubes. One advantage of this approach is that scanning of the x-ray tube can be achieved much more quickly than rotation of a mechanical gantry. Thus, views and full sets can be generated much more quickly, increasing the overall speed and throughput of the CT scanner.

Figure 1B:
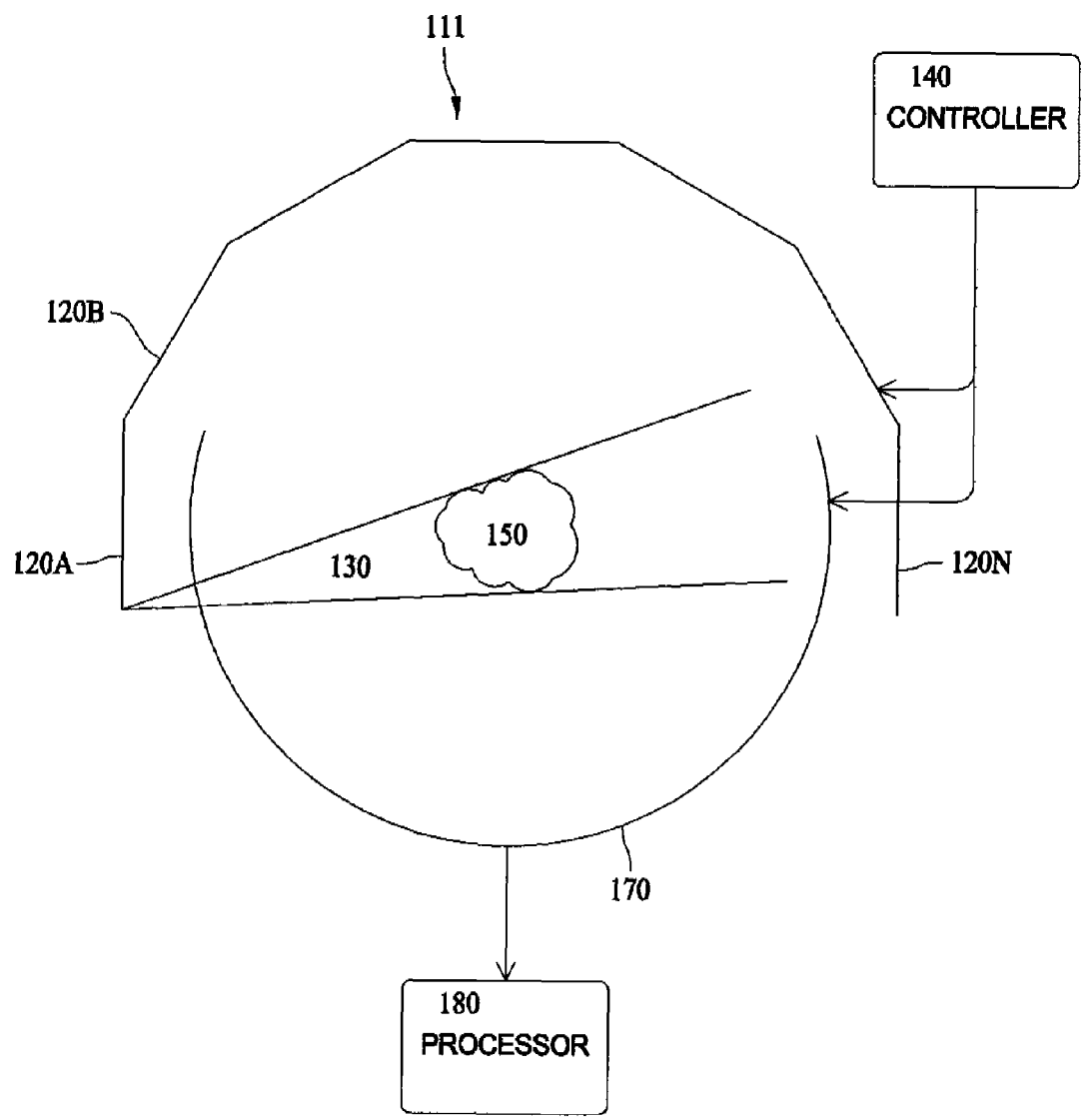

FIG. 1A is merely an example. Other implementations will be apparent. For example, the source path need not be a circular arc and the raster paths 120 also need not be circular arcs. In FIG. 1B, the raster paths 120A–N are straight lines and the source path 111 forms the sides of a polygon. Other shapes can also be used, although the source points preferably are distributed in approximately a circular arc around the object 150. Different distributions of source path to raster paths are also possible. In some cases, each raster path may be approximately the same length and/or include equal fractions of the overall source path. In other cases, different raster paths may contain different lengths or fractions of the source path.

The x-ray tubes and source points 110 may also be activated in different sequences. For example, referring to FIG. 1A, the raster paths may be activated in the sequence 112A, 112C, . . . 112M, 112B, 112D, . . . 112N, although this typically would complicate the reconstruction process. As another example, the entire raster path need not be activated at once. For example, part of raster path 112A may be activated, and then part of raster path 112B, and so on, with the remaining part of raster path 112A activated at a later time. Other sequences will be apparent.

Figure 1C:
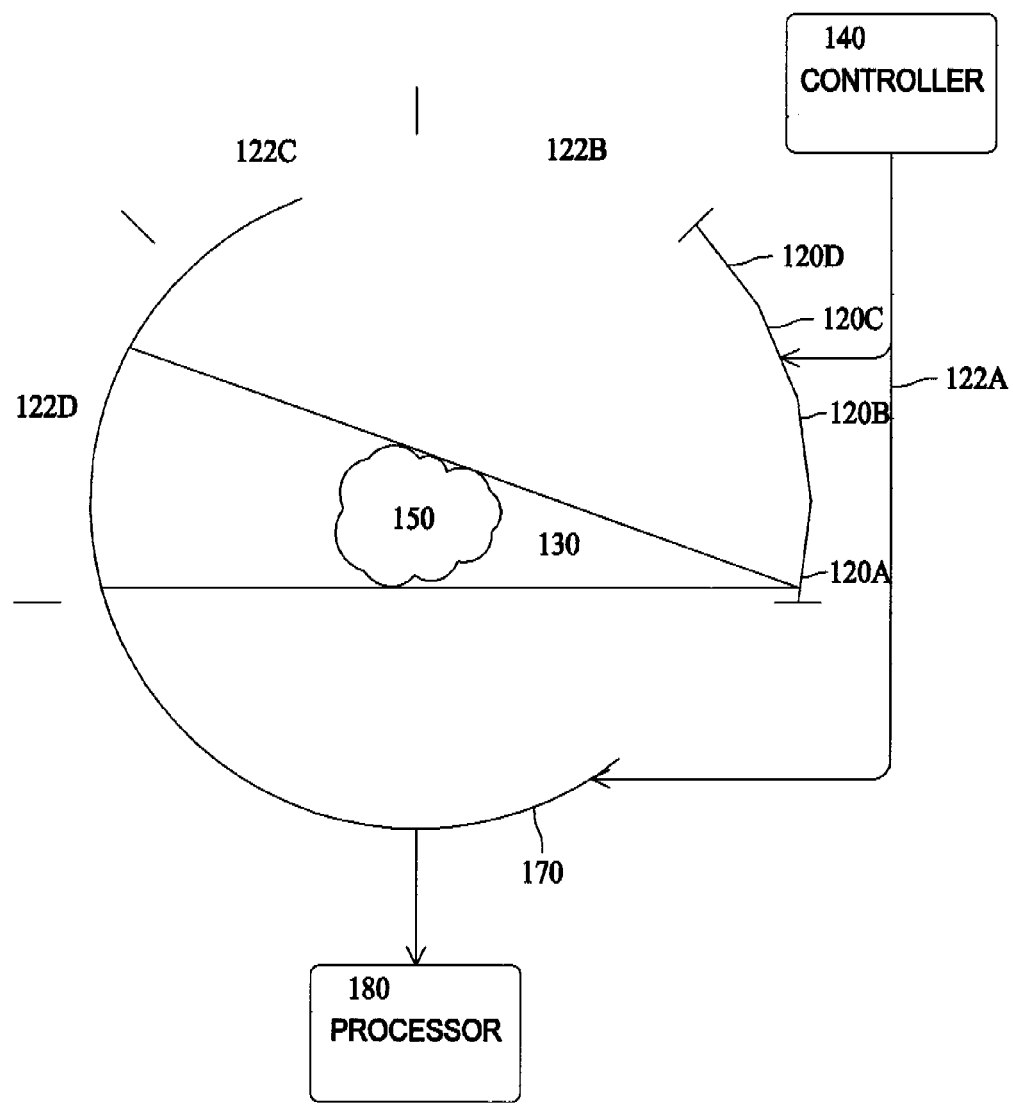
Figure 1D:
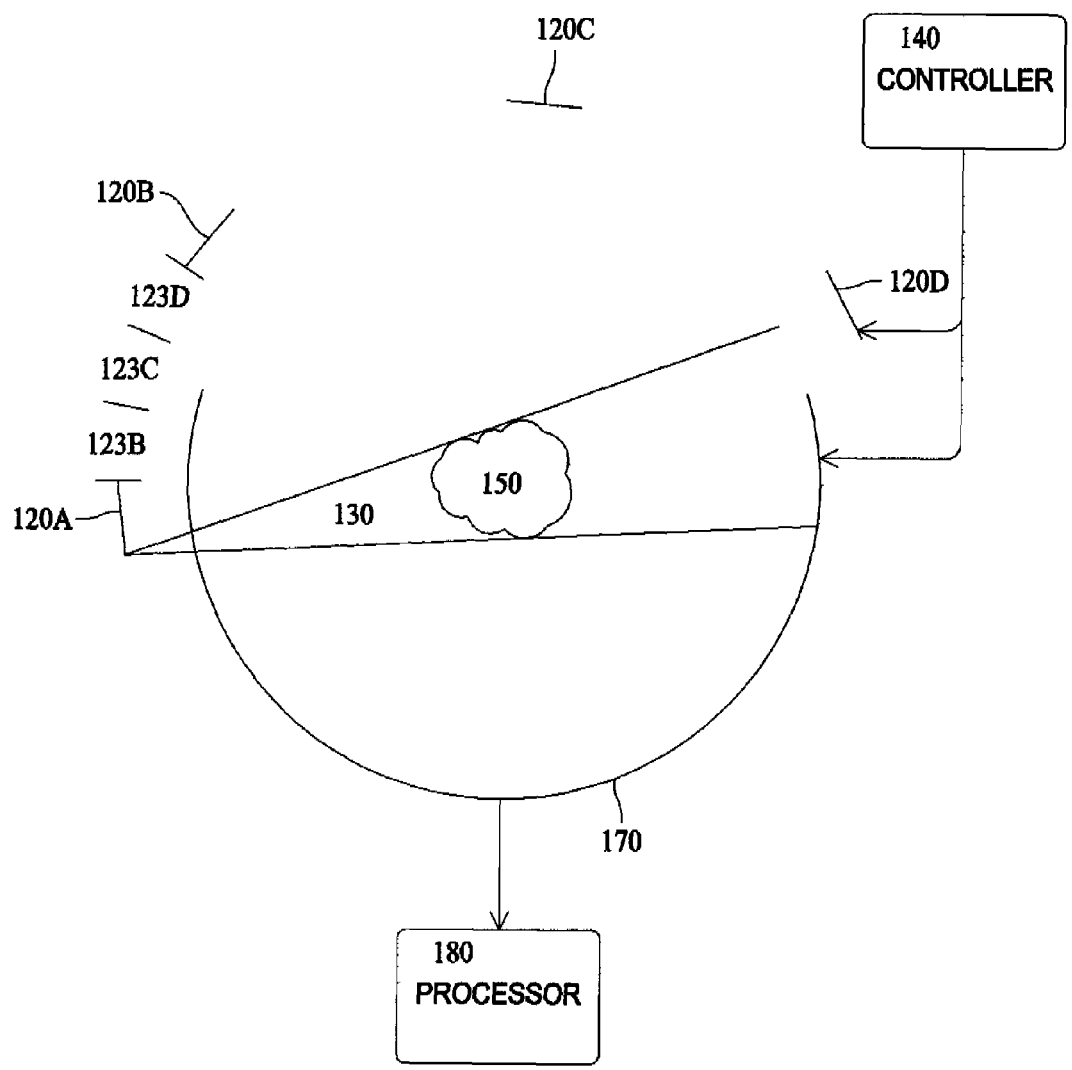

As another example, the rastered x-ray tubes and detector array 170 need not be stationary with respect to the scan plane. FIGS. 1C–1D show two examples where one or both of these components are moveable. In FIG. 1C, the raster paths 120A–D are contiguous but they are not long enough to include the entire source path. Instead, the x-ray tubes are rotated about the object to different positions 122A–122D to generate a full set of views. The detector array 170 may or may not rotate with the x-ray tubes, depending on the extent of the array. In the example of FIG. 1C, the detector array 170 is designed to rotate with the x-ray tubes. In FIG. 1D, there are gaps between the raster paths 120A–120D and the gaps are filled by rotating the x-ray tubes to different positions 123A–123D. In the figure, the labels 123B–123D show the positions of raster path 120A after rotation to these positions. The other raster paths 120B–120D would also rotate clockwise to new positions. Less angular rotation is required in FIG. 1D to complete a slice and, therefore, this approach has a potentially faster speed than the approach of FIG. 1C. However, both FIGS. 1C–1D utilize mechanical rotation, which generally is slower than the pure scanning approach shown in FIGS. 1A–1B. One advantage of FIGS. 1C–1D is that they generally utilize fewer x-ray tubes.

As a final example, FIGS. 1A–1D may give the impression that scanning of the x-ray tube is continuous, for example that an electron beam is swept in a single continuous motion from point 110A(1) to 110A(2). This is done for clarity of illustration but is not meant to be a limitation. In some implementations, the source points may be discrete (or effectively discrete), although the discrete nature can be achieved in many different ways. For example, an electron beam can be first targeted to point 110A(1) where it dwells for a period of time and generates the a corresponding x-ray fan, and then is moved instantaneously to an adjacent source point where it again dwells and generates a second x-ray fan, and so on. Alternately, the detector array 170 can be time gated, sampled or otherwise processed or filtered to effectively transform a continuous analog scan of the raster path 120 into a discrete scan. Terms such as source point, raster path and activating source points are meant to include both discrete and continuous cases.

Figure 2:
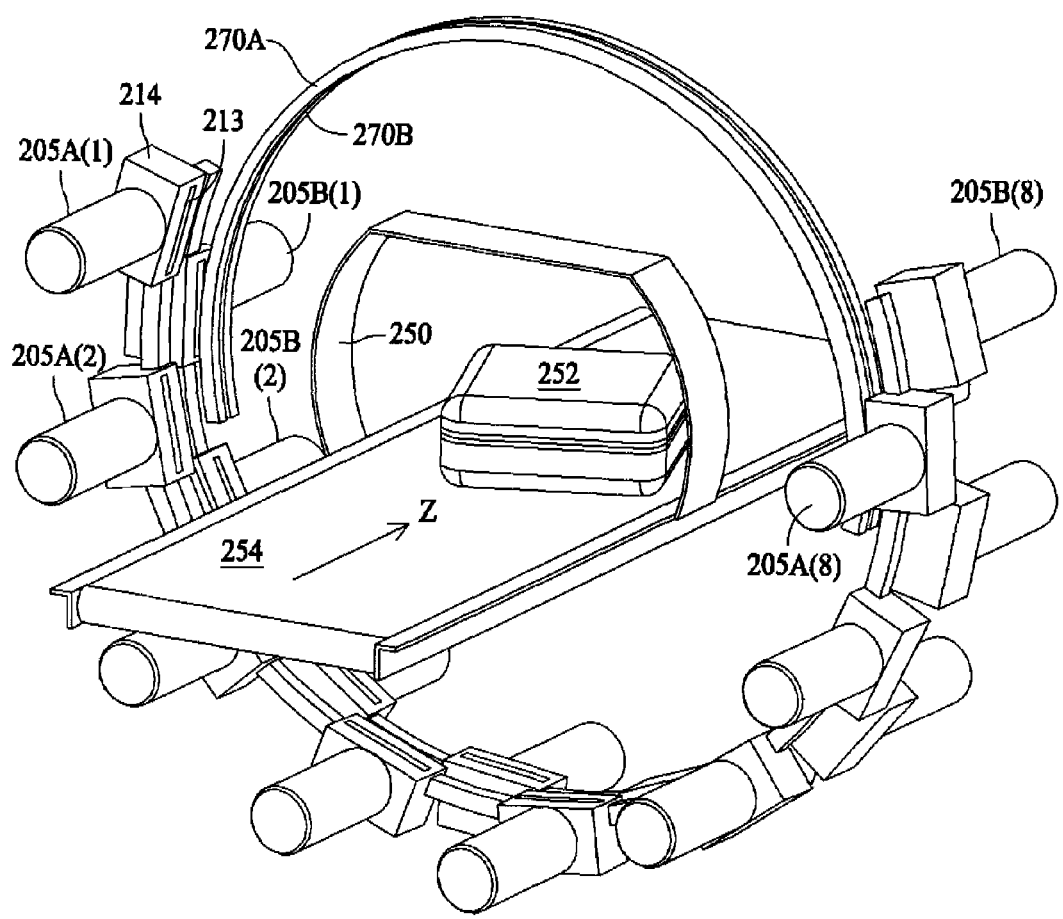
FIG. 2 is a perspective view of one embodiment of the CT scanner according to the present invention.

FIG. 2 is a perspective view of an example CT scanner according to the invention. This CT scanner is designed to scan checked bags. An opening 250 defines the target area. Checked bags 252 are moved through the target area on a conveyor belt 254 along the z direction. In medical applications, the object typically is a patient and the translation mechanism typically is a motorized table. In non-destructive testing applications, the entire geometry may be rotated by 90 degrees (i.e., scan plane is horizontal rather than vertical as shown in FIG. 2) and the object might be a rocket for example. The rastered x-ray tubes 205 and detectors 270 are grouped into two separate subscan assemblies that are located in two separate planes, denoted A and B. Eight rastered x-ray tubes 205A(1)–205A(8) and one arced detector array 270A are located in plane A. Another eight rastered x-ray tubes 205B(1)–205B(8) and arced detector array 270B are located in plane B. The x-ray tubes 205 and detectors 270 are aligned so that x-ray fans 230 projected from the A tubes are received by the A detector array, and x-ray fans projected from the B tubes are received by the B detector array. The subscan assemblies are designed so that interference between them is reduced (e.g., x-ray fans projected from A tubes do not interfere with the B detector array). For the checked bag application, given the current state of technology, CT scanners of this design preferably will have between 10–20 rastered x-ray tubes (half that number in each subscan assembly), with the raster path of each x-ray tube subtending approximately 10–30 degrees of the source path.

In this example, the x-ray tubes 205 are wider than their raster paths. Referring to x-ray tube 205A(1), the raster path is not longer than exit slit 213. However, the corresponding housing 214 is wider than the slit 213 and therefore also wider than the raster path. Accordingly, because of the physical size of the x-ray tube, if two x-ray tubes were placed adjacent to each other in the same plane, their raster paths would not be contiguous. There would be a gap in the source path which, in this example, is assumed to be unacceptable (although in some designs certain gaps can be tolerated). One solution is to position the x-ray tubes in a circular arc, but alternate between two different planes, as shown in FIG. 2. By doing this, the rasters paths for adjacent x-ray tubes can be contiguous in the scan plane because they are physically offset in the depth direction (z direction).

FIGS. 3–4 illustrate operation of this CT scanner with respect to acquiring a full set of views for one particular slice of the object. In this example, for clarity, the subscan assemblies A and B are assumed to be separated by a significant distance. As a result, subscan assembly A will produce the A views for the slice in question, then there will be a time delay to allow the slice to move from the A plane to the B plane, and then subscan assembly B will produce the B views for the slice. In the following explanation, only the x-ray fans that are relevant to this particular slice will be described. However, this does not mean that the subscan assemblies A and B are inactive at all other times, as they may be producing views for other slices.

Figure 3A:
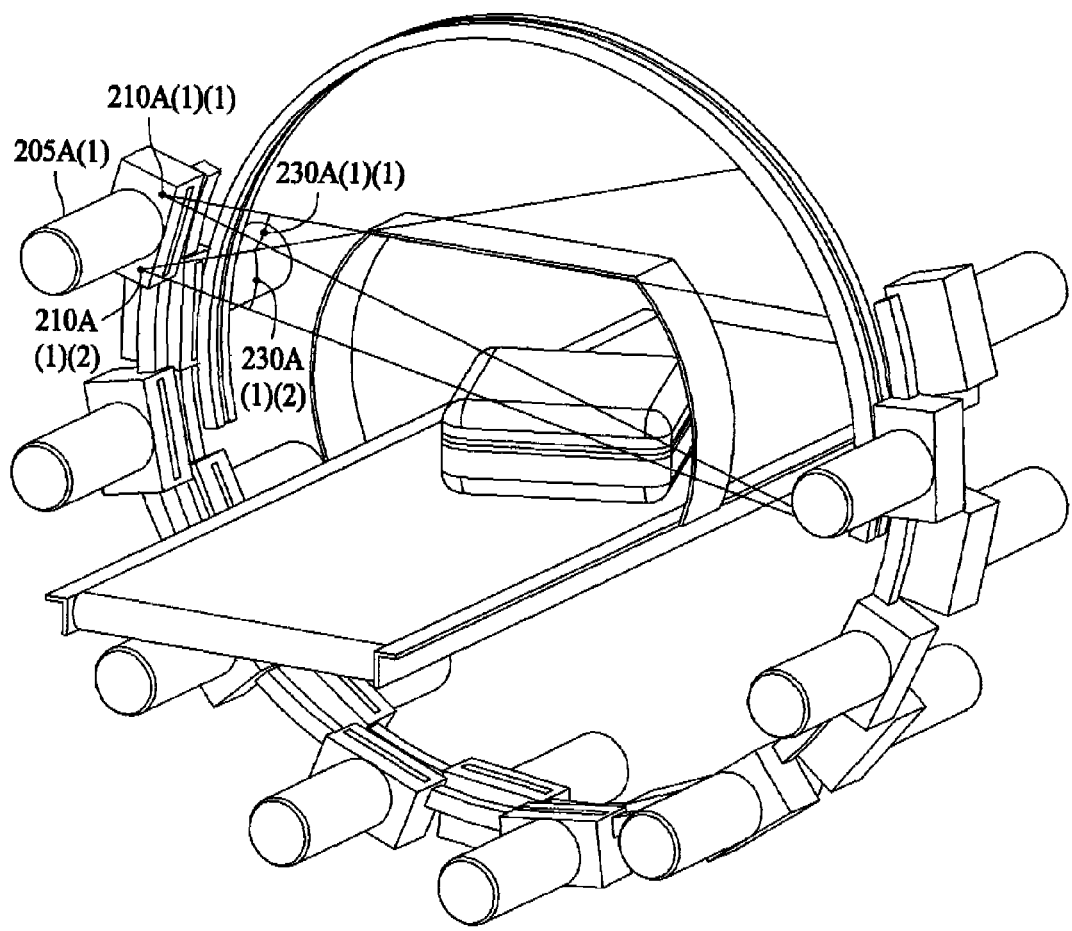
FIGS. 3A–3C are perspective views illustrating operation of the CT scanner of FIG. 2.
Figure 3B:
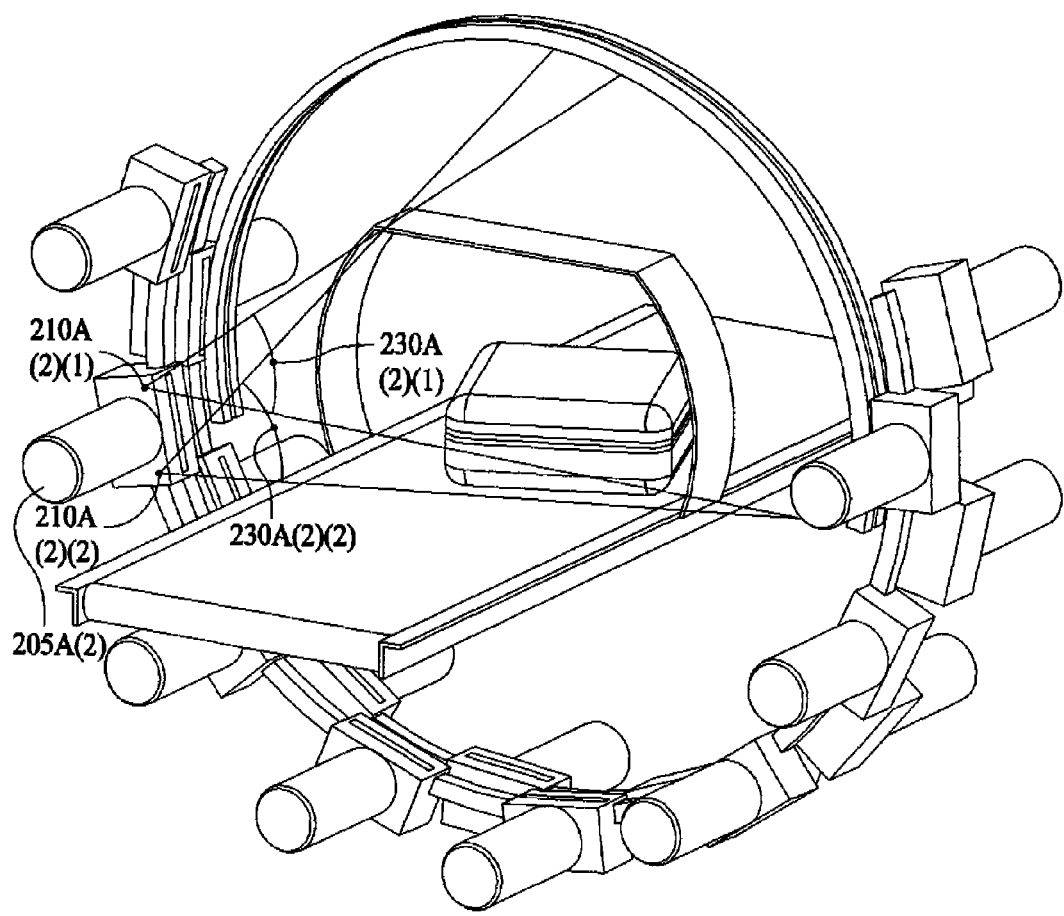
Figure 3C:
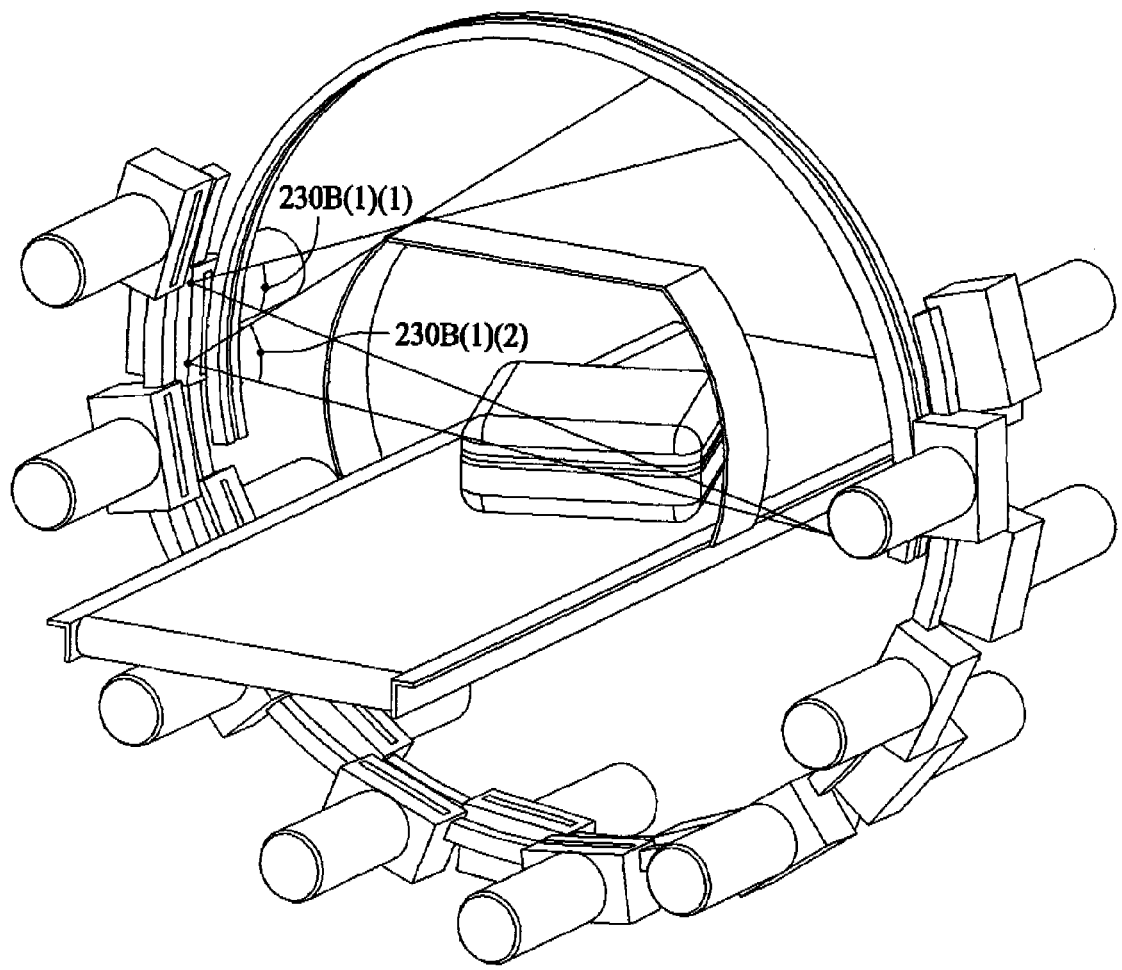

In FIGS. 3A–3C, only the relevant part of each x-ray fan 230 is shown for clarity. To produce the views that are relevant to one particular depth location on the object, the A x-ray tubes 205A are activated sequentially from tube 205A(1) to 205A(8). When each x-ray tube is activated, the source points within that tube are also activated sequentially, also in a counterclockwise direction. Thus, the scan of a slice begins by activating x-ray tube 205A(1) and activating source points 210A(1)(1)–210A(1)(2), sequentially producing x-ray fans 230A(1)(1)–230A(1)(2), as shown in FIG. 3A. This produces some of the views required for the full set of views for this particular slice. X-ray tube 250A(2) is activated next, sequentially producing x-ray fans 230A(2)(1)–230A(2)(2) from source points 210A(2)(1)–210A(2)(2), as shown in FIG. 3B. This process repeats to x-ray tube 250A(8). When plane A is completed, approximately half of the full sets of views for this particular depth location have been generated by subscan assembly A.

Figure 4A:
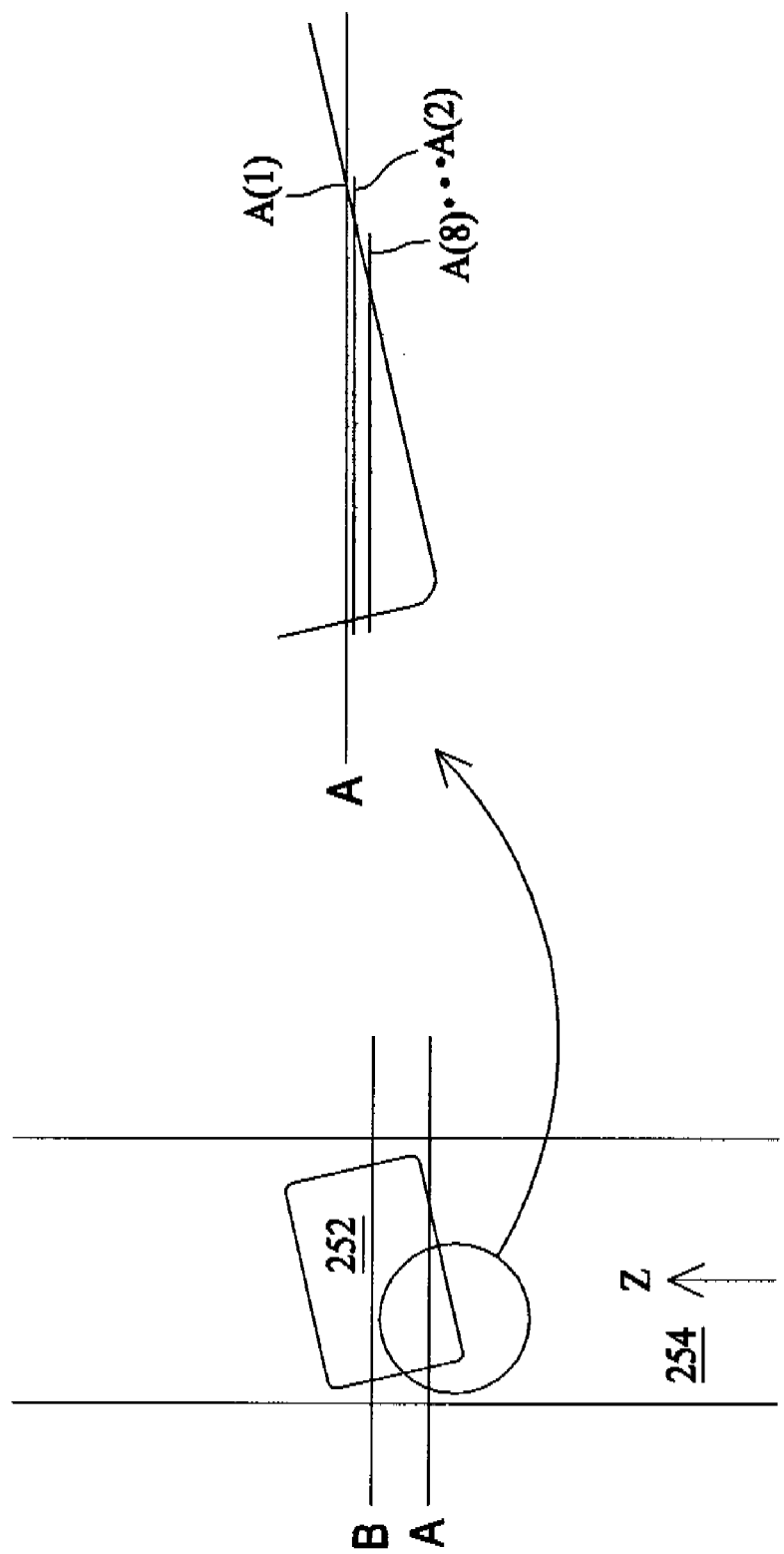
FIGS. 4A–4B are simplified top views illustrating operation of the CT scanner of FIG. 2.

Since the bag 252 is continuously moving, this procedure results in a spiral scan of the bag. X-ray tube 250A(1) will scan a slightly different plane of the bag than x-ray tube 250A(8). The left-hand side of FIG. 4A shows a top view of the bag 252 on conveyor belt 254, with planes A and B marked as lines. The right-hand side of FIG. 4A is a magnification of the circled part, showing the intersection of the bag with plane A. In FIG. 4A, the bag 252 has moved to a position where the first x-ray tube in plane A is activated. The source points within x-ray tube 205A(1) will interrogate the plane marked A(1) in FIG. 4A, x-ray tube 205A(2) will interrogate plane A(2) and so on up to plane A(8). These planes are slightly offset from each other due to movement of the bag. The planes A(2)–A(8) are marked in the magnified view within FIG. 4A but each plane is not actually interrogated until the bag moves so that the plane A(2)–A(8) is aligned with plane A of the subscan assembly. In addition, the spacing between planes A(1)–A(8) is exaggerated in FIG. 4A to show the effect of bag movement and the resulting spiral scan.

Figure 4B:
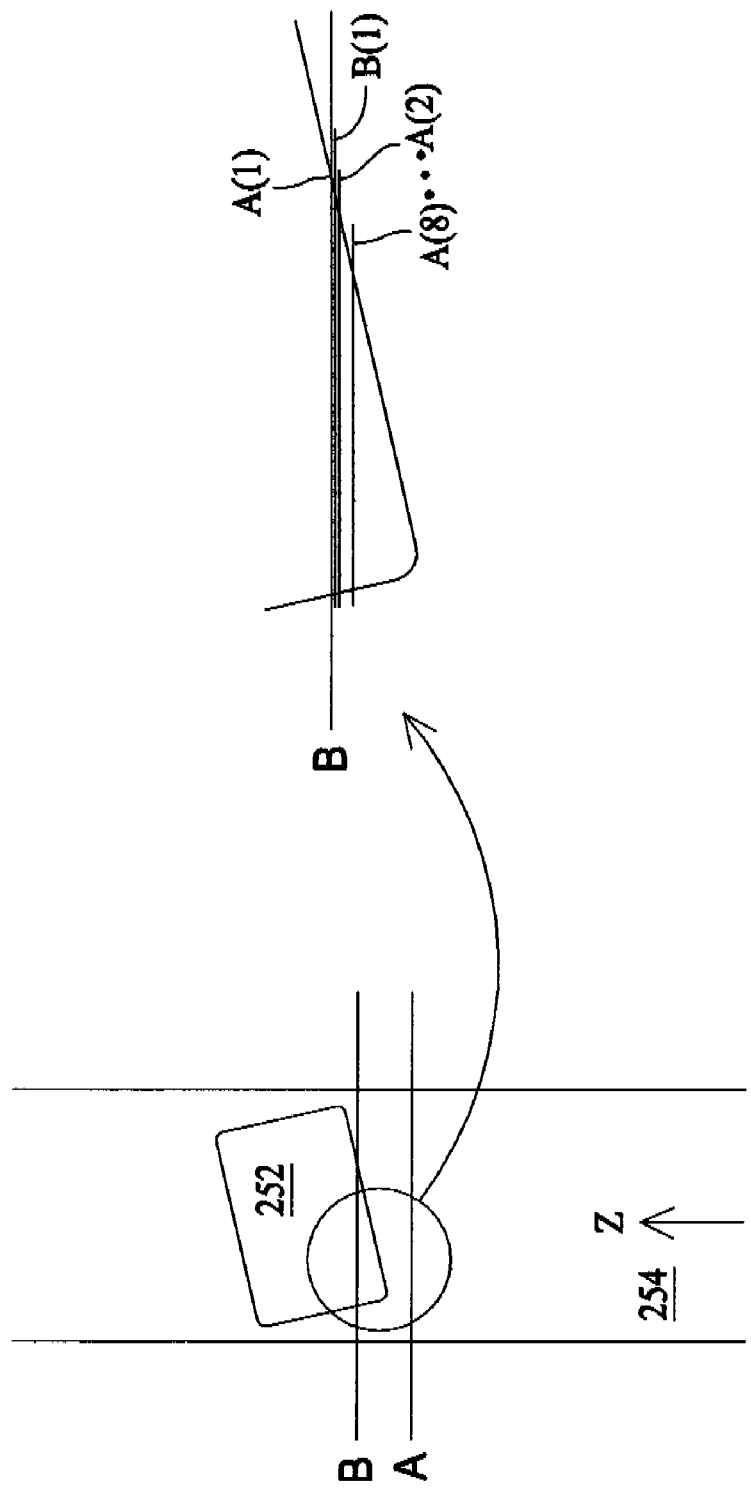

Returning now to FIG. 3, the remaining views in the full set for a particular depth location are generated by subscan assembly B. However, in this example, assembly B is offset in the z direction with respect to assembly A. The controller synchronizes the x-ray tubes with the motion of the object 250 to compensate for this offset. In FIG. 3C, the bag 252 has moved so that the slice of the bag that was previously interrogated by assembly A is now in plane B. At this point, the B x-ray tubes and source points are activated to generate the remaining views for this particular slice. FIGS. 3C and 4B show the beginning of this sequence. In FIG. 3C, x-ray tube 205B(1) produces x-ray fans 230B(1)(1)–230B(1)(2). The remaining x-ray tubes 205B(2)–205B(8) are activated in sequence. In FIG. 4B, the bag 252 has moved to a position where x-ray tube 205B(1) is activated. As shown in the magnified views, x-ray tube 205B(1) interrogates plane B(1), which is located between planes A(1) and A(2). This is because in the circular arc, x-ray tube 205B(1) is located between x-ray tubes 205A(1) and 205A(2). This synchronization preserves the spiral scan of object 250.

The above explanation described the generation of a full set of views for one particular slice. However, the bag contains many different slices and, if the subscan assemblies are separated by a significant distance, then the slices typically are not generated one full set at a time. In other words, typically, the full set of views for one slice is not completed before views for the next slice are begun. Thus, although each slice may have an activation sequence of A(1)–A(8), B(1)–B(8), when all slices are taken into account, the actual activation sequence may be different. For example, if only one tube is activated at a time, the sequence may be A(1), B(1), A(2), B(2), etc., with the A and B tubes interrogating different depth locations. Alternately, if the subscan assemblies are close enough together, this same sequence may be used to interrogate a single slice.

Figure 5A:
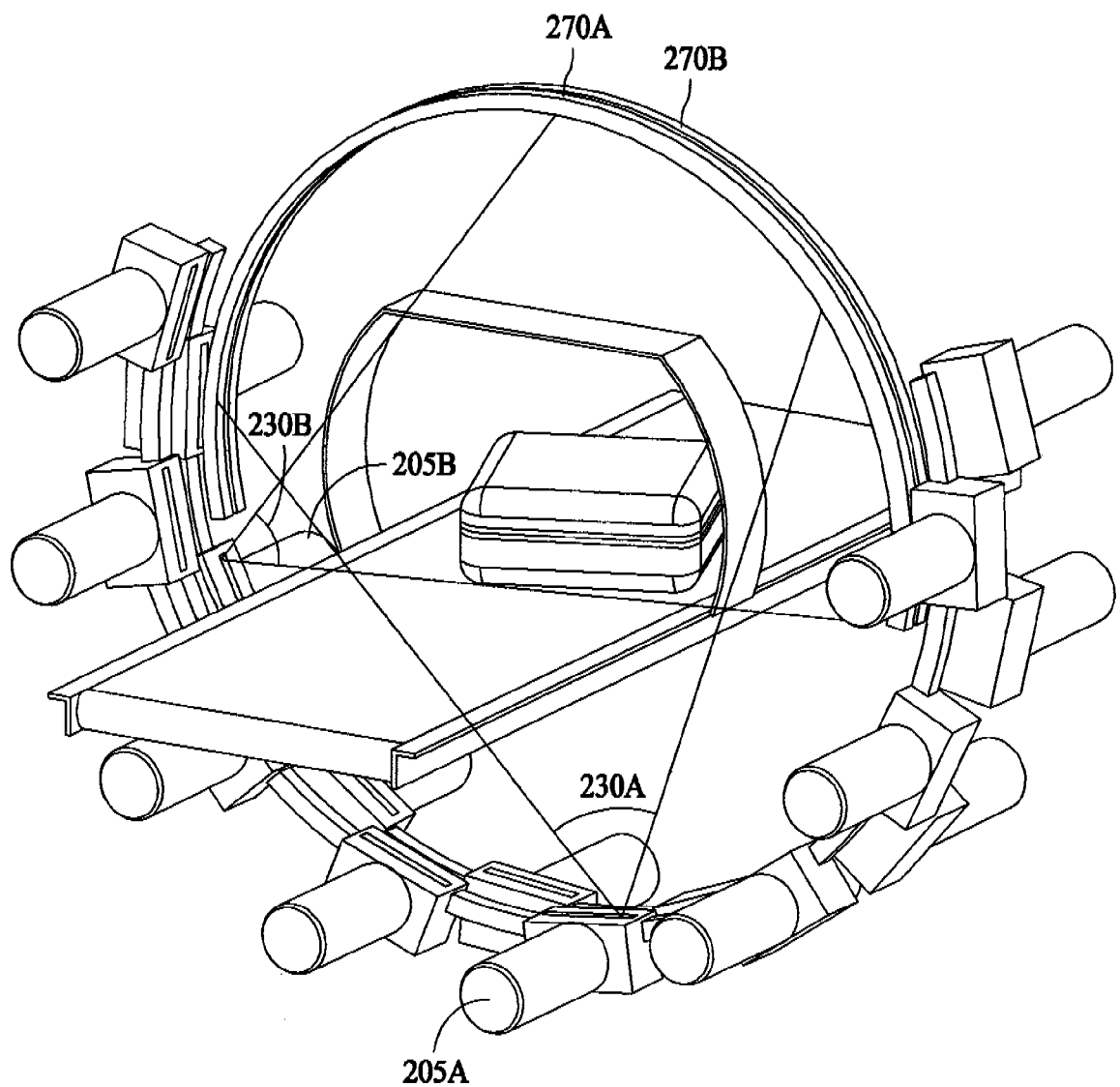
FIGS. 5A–5B are a perspective views illustrating other aspects of operation of the CT scanner of FIG. 2.

In the description of FIGS. 3–4, only one x-ray fan was generated at a time. This was done for purposes of clarity and is not a requirement. Multiple x-ray fans can be generated simultaneously so long as they do not adversely interfere with each other and this will generally be the case. The A subscan assembly can scan at the same time as the B subscan assembly, although each assembly would be interrogating different parts of the bag due to the z offset between the two assemblies. For example, FIG. 5A shows a situation where an A tube 205A and a B tube 205B are activated simultaneously. The x-ray fan 230A from the A tube is generating a view for one part of the object and the x-ray fan 230B from the B tube is generating a view for a different part of the object. In this case, the A and B planes have been designed so that the A x-ray fans 230A do not interfere with the B detectors 270B, and vice versa. In addition, the A and B assemblies could be out of phase with each other. As shown in FIG. 5A, when the A assembly is at the beginning of a scan, the B assembly is in the middle of a scan. This further reduces interference between the two assemblies since different parts of the detector array will be active for each assembly. In this case, the synchronization would be different from the previous case.

Figure 5B:
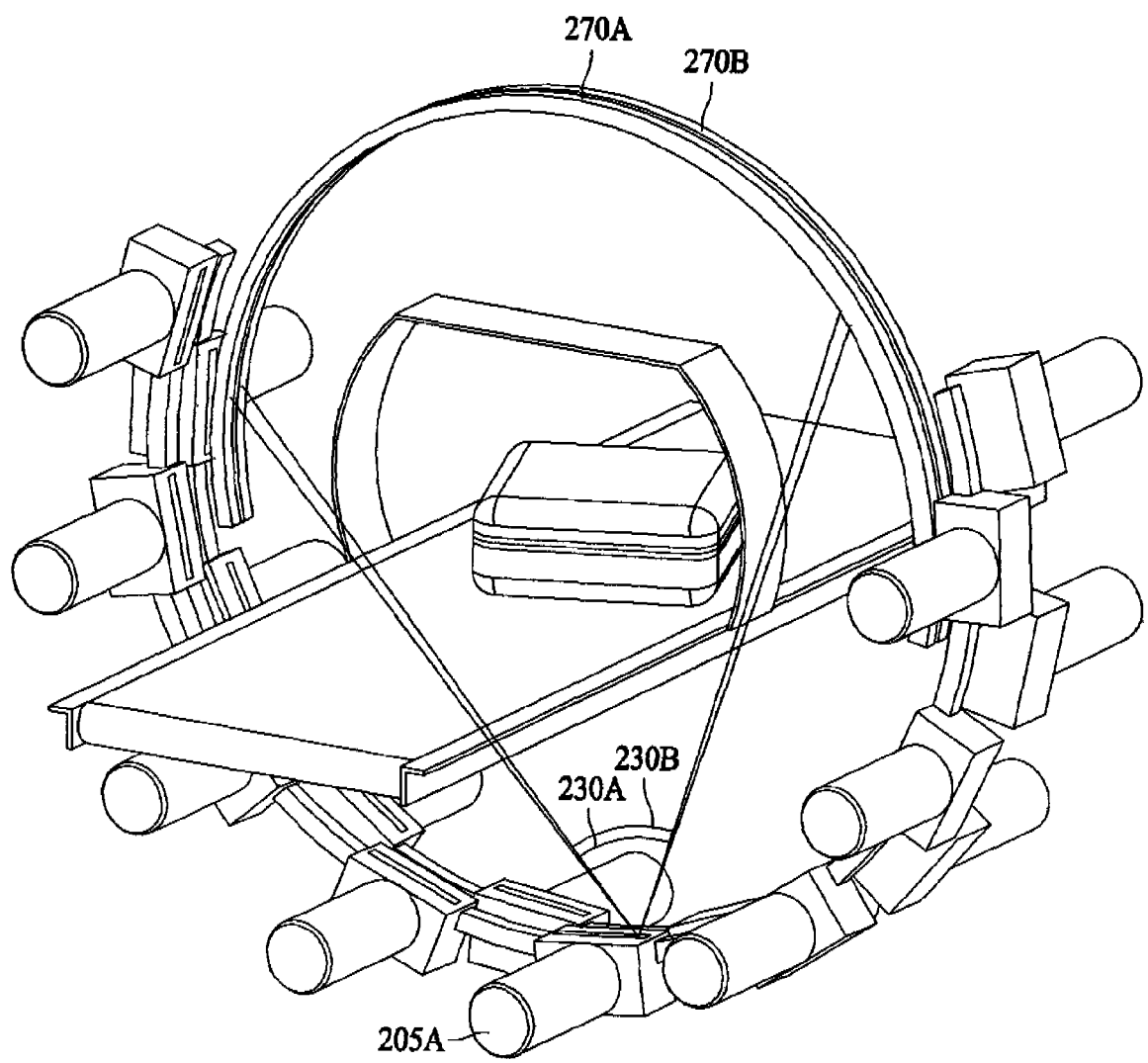

In an alternate approach, rather than activating both assemblies simultaneously, in some cases, the x-ray tubes can be activated one at a time, with each x-ray tube simultaneously generating views for two different slices though the object. For example, FIG. 5B shows a situation where only an A tube 205A is active but it generates x-ray fans 230A and 230B that are received by both detector arrays 270A and 270B, thus generating two separate slices (or the equivalent in the case of a spiral scan). More detector arrays can be used in order to generate more than two slices simultaneously. FIG. 5B is used to illustrate the general principle. In practice, rather than having two discretely separated detector arrays 270A–270B, a single detector assembly can be made of multiple rows of detectors with very little separation (fraction of mm) between rows. This results in slices with small gaps. Note that since the x-ray tubes 205A and 205B are separated in the depth direction, they will be interrogating slices that are inclined at slightly different angles. Preferably, the separation between the x-ray tubes 205A and 205B is small enough that this difference is negligible or can be corrected for.

Figure 6:
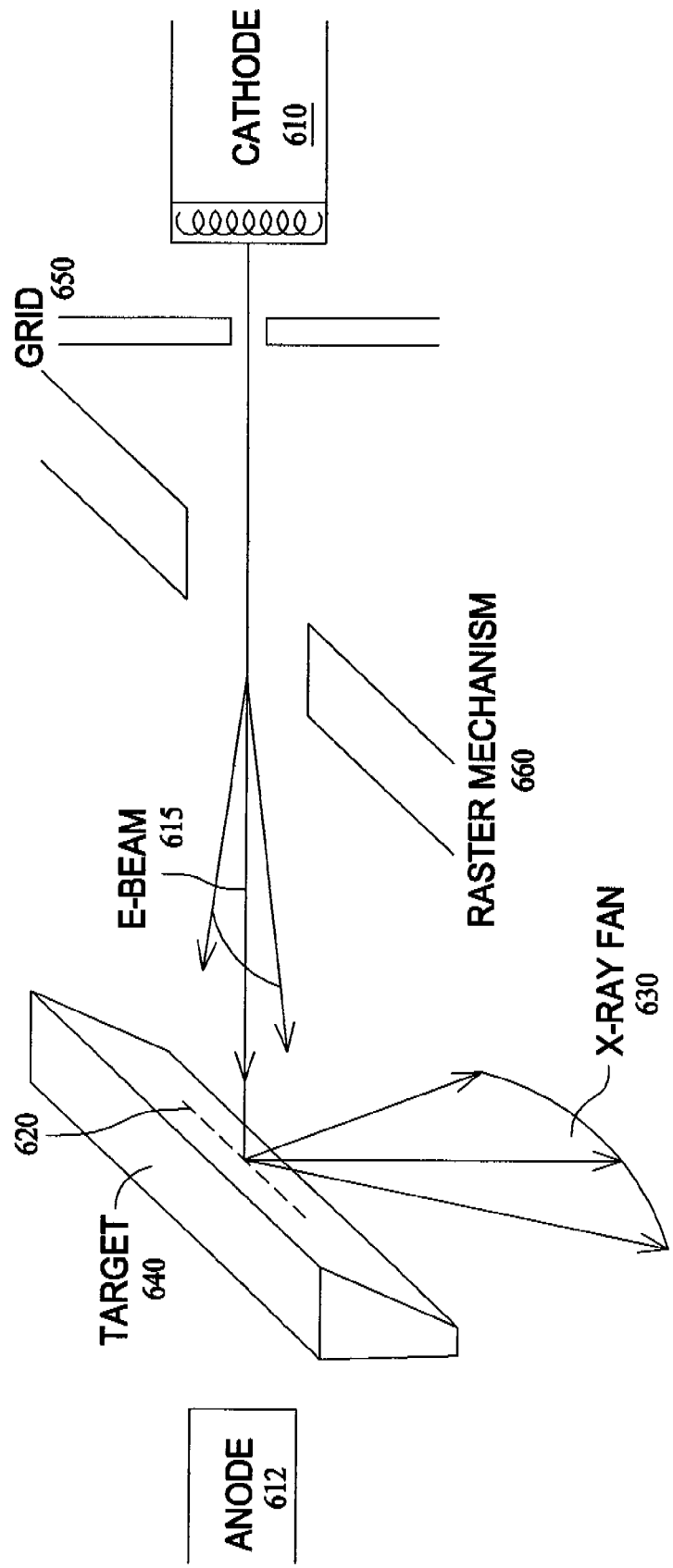
FIG. 6 is a diagram of a rastered x-ray tube suitable for use with the invention.

FIG. 6 is a simplified diagram of an electron rastered x-ray tube suitable for use with the invention. In this design, a cathode 610 (e.g., a filament) generates electrons and the resulting electron beam 615 is accelerated towards anode 612 (the target is the anode). The electron beam 615 hits a target 640 (which may be the anode itself), which generates the x-rays for the x-ray fan 630. A raster mechanism 660 deflects the electron beam 615 to different points on the target 640, resulting in x-ray fans emanating from different source points. The raster mechanism 660 preferably is based on either electrical or magnetic deflection. The set of addressable points acts as the raster path 620 for the x-ray tube. A grid 650 is used to turn the electron beam 615 on and off. When the grid 650 is properly biased, the grid 650 will halt the flow of electrons from cathode 610 to anode 612. The electron beam 615 is prevented from reaching the target 640. One advantage of using a grid 650 is that the cathode 610 is always on and no warm-up period is required. This is necessary if the x-ray tube is activated and deactivated quickly. In an alternate approach, the electrons are produced by field emission instead of the thermionic process. In this case, there is no need for a grid because the response time of the field emission source is very fast.

In operation, to activate the x-ray tube of FIG. 6, a controller switches off the grid 650 (i.e., biases the grid to allow the electron beam to propagate). The controller also controls the raster mechanism 660 to deflect the electron beam 615 to the proper source point(s) on the target 640.

In one approach, the raster mechanism 660 is continuously sweeping and the controller controls rastering by timing the switching of grid 650. For example, if the raster path 620 is to be scanned from far left to far right, the controller waits until the raster mechanism 660 would deflect the electron beam 615 to the far left and then turns the grid 650 off. The electron beam 615 then hits the target 640 on the far left and over time is scanned to the far right by the automatic sweeping of the raster mechanism. When the raster mechanism reaches the far right, the controller turns the grid 650 back on, turning off the electron beam 615.

One advantage of the approach described above is its speed. There is no mechanical rotation. The movement of the source point along a source path is achieved solely by switching grids 650 on and off and by the raster mechanisms 660. As a result, much faster scanning can be achieved. For the baggage inspection example, effective rotational frequencies in excess of 1000 RPM acquiring 500–1000 views per slice should be attainable. At this speed, a belt speed of 0.5 meter per second or higher could be maintained, yielding 500–1000 slices per bag and throughput in excess of 1000 bags per hour.

Figure 7:
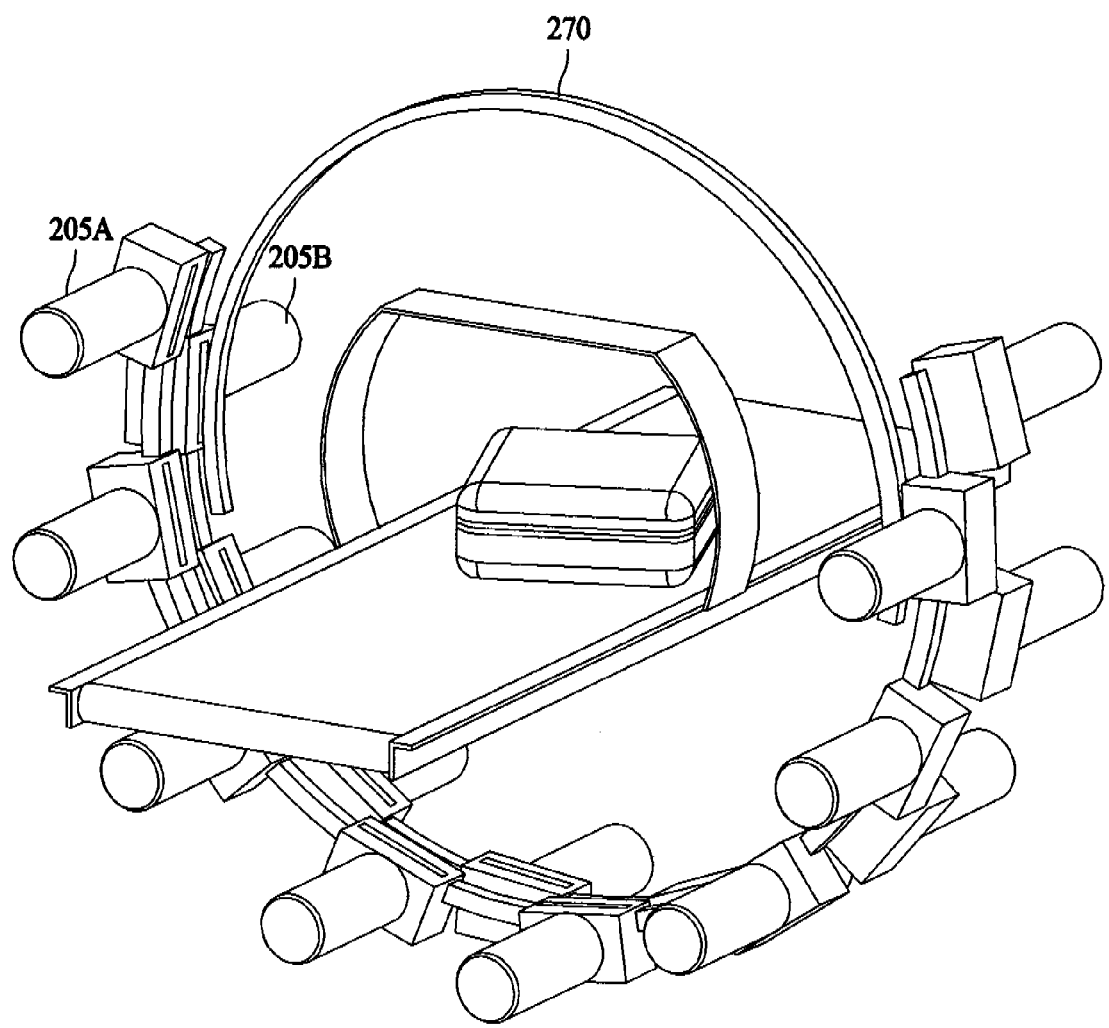
FIG. 7 is a perspective view of another CT scanner according to the present invention.

Although the detailed description contains many specifics, these should not be construed as limiting the scope of the invention but merely as illustrating different examples and aspects of the invention. It should be appreciated that the scope of the invention includes other embodiments not discussed in detail above. For example, FIG. 7 shows a CT scanner with two arrays of x-ray tubes 205A and 205B but only one detector array 270. In this example, the x-ray tubes are activated one at a time, with both arrays of x-ray tubes sharing the detector array 270.

Figure 8:
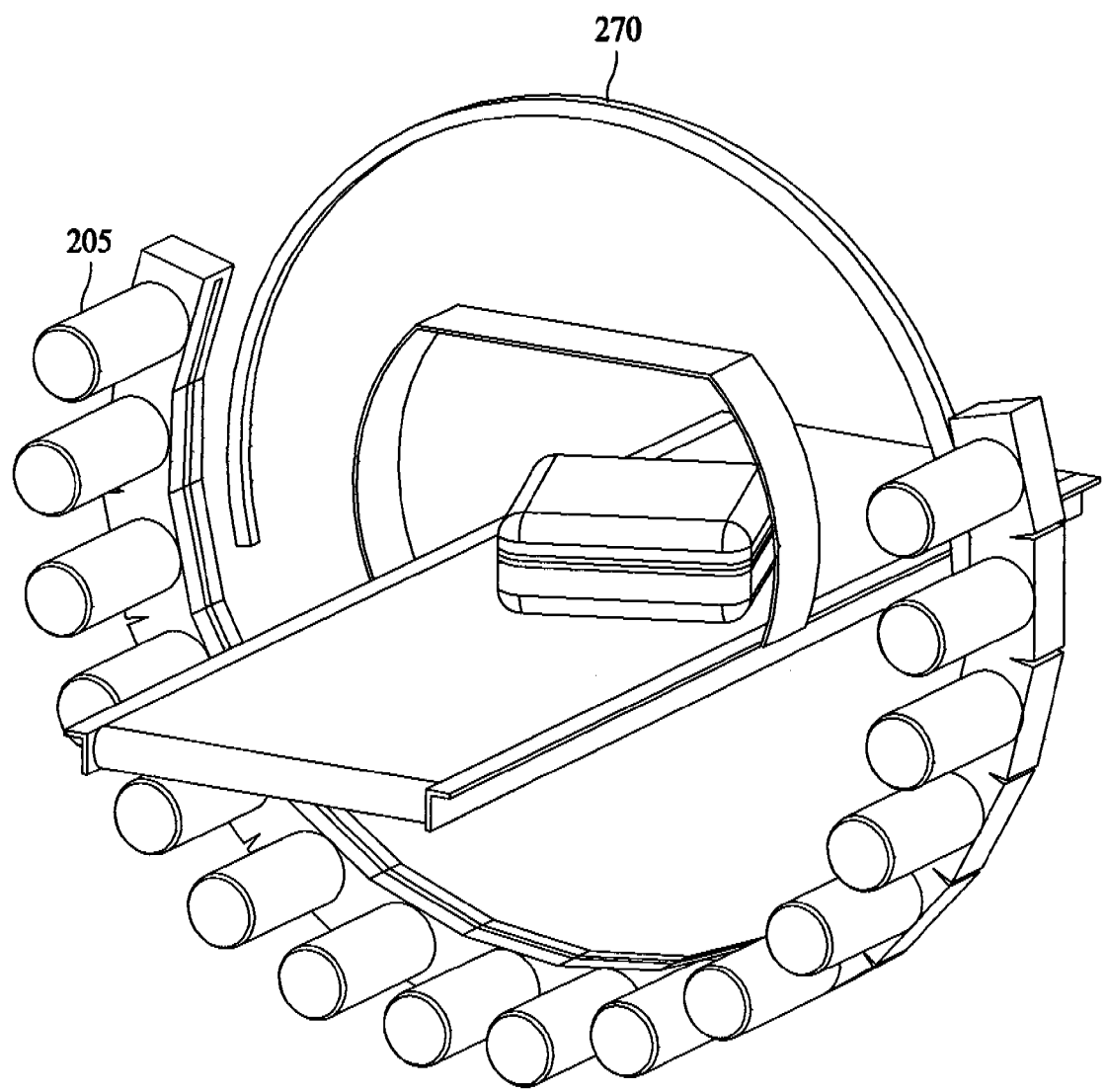
FIG. 8 is a perspective view of another CT scanner according to the present invention.

As another example, FIG. 8 shows a CT scanner where the x-ray tubes 205 are all located in a common plane. Here, the x-ray tubes are designed so that their raster paths can be contiguous, thus forming a continuous or nearly-continuous source path. This example shows a single detector array 270, although multiple detector arrays can be used to capture multiple slices simultaneously. In addition, the x-ray tubes and detector arrays can be designed to compensate for cone beam error, as described in U.S. Pat. No. 6,735,271, which cone beam correction is incorporated herein by reference. The tubes and detector arrays may also be designed to produce a planar slice of a constantly moving object, as described in U.S. Pat. No. 6,735,271, which planar slice geometry is incorporated herein by reference. As another variation, the scan plane need not be vertical. It can be horizontal or oriented in other directions. In addition, even if the x-ray tubes are stationary with respect to the scan plane, they may be moveable in the depth direction. For example, an entire scan or subscan assembly may be translated relative to the object to image different slices within the object (as opposed to moving the object relative to the scan assembly).

Figure 9:
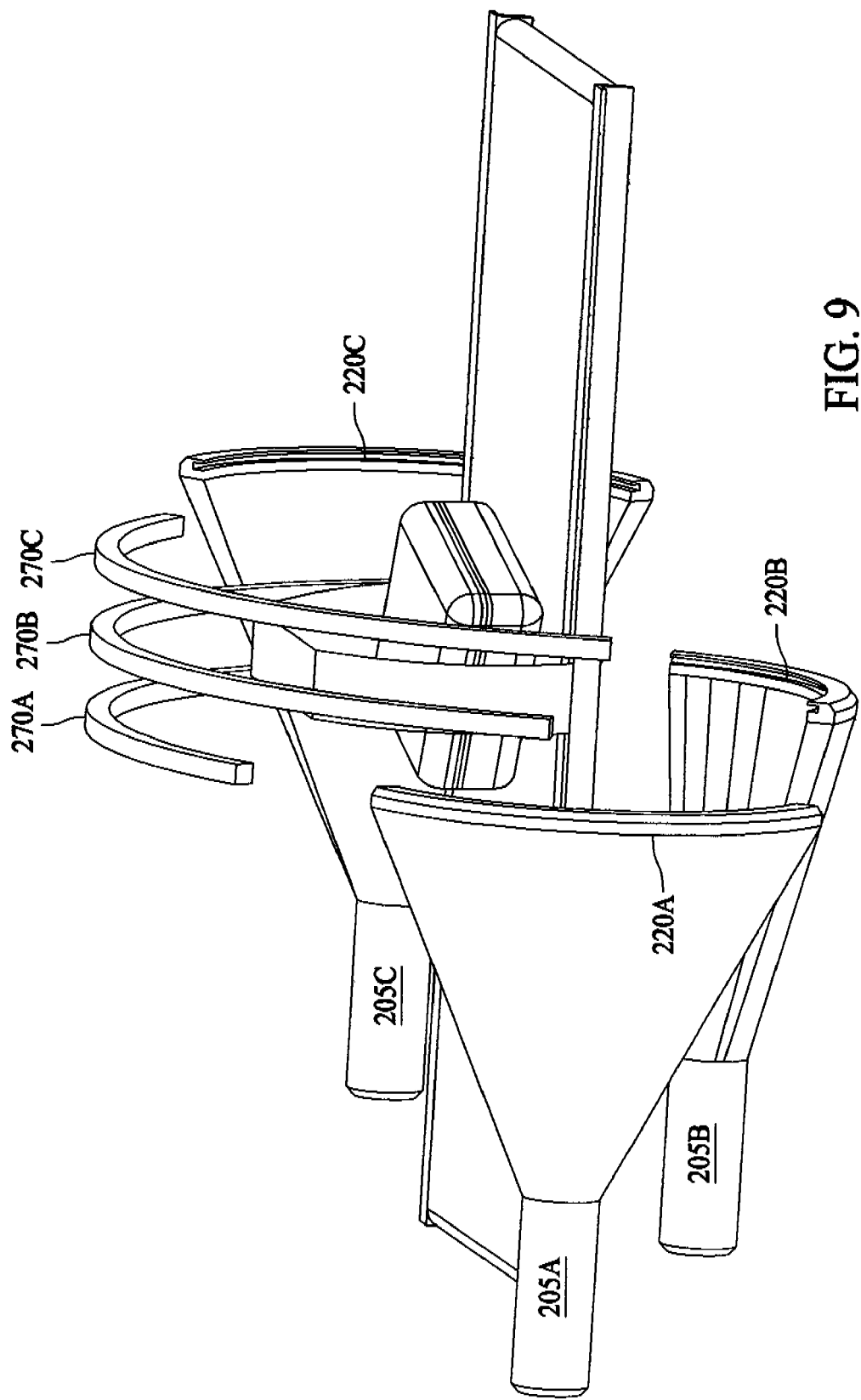
FIG. 9 is a perspective view of another CT scanner according to the present invention.

FIG. 9 shows another CT scanner which reduces the number of x-ray tubes and increases the size of each tube relative to the previous examples. Here, there are three x-ray tubes 205A–205C and the raster path 220A–220C for each x-ray tube covers a significant portion of the overall source path. In this example, each x-ray tube 205A–205C has a corresponding detector array 270A–270C in the same plane as the tube's raster path 220A–220C. Each tube/detector assembly is offset in the depth direction so that collimation at the detector can remove scattered x-rays from the other tubes, allowing simultaneous scanning of all tubes. The scanned object moves on a conveyor belt or other transport mechanism past the plane of each tube/detector subscan assembly. A controller synchronizes the scanning of the raster path for each subscan assembly with the movement of the object so that each scan starts at the same depth in the object. In a preferred design, each tube scans continuously, interrogating successive planes of the scanned object.

As a final example, the electron beam 615 can be generated by field emission or other approaches rather than by the approach shown in FIG. 6. In addition, the x-ray generator can be operated at different accelerating voltages and/or at one or more filtrations to emit different x-ray spectra. Thus, the attenuation dependency (or other types of information) as a function of x-ray spectra can also be sensed.

On the processing side, rather than capturing full sets by synchronizing different detector arrays and/or subscan assemblies, different views can be captured at different depths of the object, with each view (or set of views) tagged with the corresponding depth. Full sets can be assembled separately from the data acquisition based on the depth tags. For example, if the image for a particular depth is desired, the views for the relevant depths can be retrieved and the image reconstructed from the retrieved records.

Furthermore, conventional aspects of the CT scanners are not illustrated. For example, referring to FIG. 2, high voltage power can be distributed to the x-ray tubes using conventional techniques. In one approach, hubs are used to distribute the high voltage. Each hub provides power directly to each x-ray tube that it services. The topology is a star configuration with the hub at the center and a direct power feed to each x-ray tube. In a different approach, the high voltage is distributed using a bus topology. There is a central distribution line and each x-ray tube taps power from the central line. Cooling can be achieved using similar topologies. Alternately, each x-ray tube can be cooled independently by its own dedicated heat exchanger.

Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. A CT scanner for scanning an object by projecting x-ray fans from source points located along a source path to generate multiple views of the object, the CT scanner comprising a plurality of rastered x-ray tubes located in fixed positions in one or more scan planes, each rastered x-ray tube characterized by a raster path and capable of producing x-ray fans projected from different points along the raster path, wherein substantially all of the source points along the source path of the CT scanner are located on at least one of the raster paths of the x-ray tubes, wherein each x-ray tube is positioned such that the raster paths of adjacent x-ray tubes are substantially continuous.

2. The CT scanner of claim 1 wherein the raster path of each x-ray tube is approximately the same length.

3. The CT scanner of claim 1 wherein the plurality of x-ray tubes consists of approximately 10–20 x-ray tubes.

4. The CT scanner of claim 3 wherein the raster path of each x-ray tube subtends between approximately 10–30 degrees of the source path.

5. The CT scanner of claim 1 wherein the plurality of x-ray tubes consists of approximately 3–5 x-ray tubes.

6. The CT scanner of claim 1 wherein the x-ray tubes are grouped into at least two subscan assemblies defining at least two scan planes that are offset with respect to each other along a depth direction.

7. The CT scanner of claim 6 further comprising:
a mechanism for moving the object relative to the subscan assemblies along the depth direction; and
a controller for synchronizing activation of source points along the source path to the relative motion of the object, wherein the synchronization compensates for the offset of the subscan assemblies along the depth direction.

8. The CT scanner of claim 6 comprising:
a mechanism for moving the object relative to the subscan assemblies along the depth direction; and
a controller that records a corresponding depth for views acquired by the subscan assemblies.

9. The CT scanner of claim 6 wherein the x-ray tubes are positioned approximately in a circular arc about the object and alternate between the subscan assemblies.

10. The CT scanner of claim 6 wherein a physical size of the x-ray tubes prevents raster paths of adjacent x-ray tubes from being contiguous in a same plane.

11. The CT scanner of claim 6 further comprising:
a detector array positioned to receive x-ray fans from the x-ray tubes; and
a controller for activating not more than one x-ray tube at a time.

12. The CT scanner of claim 6 further comprising:
at least two detector arrays, each positioned to received x-ray fans from the x-ray tubes; and
a controller for activating not more than one x-ray tube at a time, wherein separate x-ray fans from the x-ray tube are received simultaneously by the detector arrays.

13. The CT scanner of claim 6 further comprising:
at least two detector arrays, each detector array positioned to receive x-ray fans from the x-ray tubes in the corresponding subscan assembly; and
a controller for simultaneously activating x-ray tubes from different subscan assemblies, each x-ray tube producing an x-ray fan received by the corresponding detector array.

14. The CT scanner of claim 1 wherein the x-ray tubes comprise:
a target, wherein the raster path of the x-ray tube is located on the target;
a source for generating an electron beam directed towards the target; and
a raster mechanism for rastering the electron beam to direct points along the raster path on the target.

15. The CT scanner of claim 14 wherein the x-ray tubes further comprise:
a grid located between the source and target for switchably preventing the electron beam from reaching the target.

16. The CT scanner of claim 14 wherein the source generates electrons by field emission.

17. The CT scanner of claim 1 wherein the x-ray tubes are operated at different accelerating voltages to produce x-ray fans of different energies.

18. The CT scanner of claim 1 wherein the x-ray tubes are operable to produce x-ray fans of at least two different x-ray spectra.

19. The CT scanner of claim 1 wherein the object is a checked bag.

20. The CT scanner of claim 1 wherein the object is a carry-on item.

21. The CT scanner of claim 1 wherein the object is air break bulk cargo.

22. The CT scanner of claim 1 further comprising:
a controller for activating source points along the source path at a rate sufficient to scan at least 1000 objects per hour.

23. The CT scanner of claim 1 further comprising:
a controller for activating the x-ray tubes in a predetermined sequence.

24. The CT scanner of claim 1 further comprising:
a controller for activating the source points along the source path at a rate sufficient to generate a full set of views in less than 0.1 second.

25. The CT scanner of claim 1 further comprising:
a detector array positioned to receive the x-ray fans projected from the source points.

26. The CT scanner of claim 25 wherein the detector array comprises charge integration electronics.

27. The CT scanner of claim 25 wherein the detector array comprises single-photon counting electronics.

28. The CT scanner of claim 25 wherein the detector array comprises energy-sensitive detectors.

29. The CT scanner of claim 25 wherein the detector array comprises stacked detectors.

30. The CT scanner of claim 1 further comprising:
a controller for activating the source points along the source path in a manner to generate slices of the object.

31. The CT scanner of claim 1 further comprising:
a controller for activating the source points along the source path in a manger to generate a spiral scan of the object.

32. The CT scanner of claim 1 further comprising:
a mechanism for moving the object relative to the CT scanner along the depth direction; and
a detector array positioned to receive the x-ray fans projected from the source points, wherein the source path and the detector array form sections of helixes such that a scan of the moving object results in planar scan of the object.

33. The CT scanner of claim 1 further comprising:
at least two detector arrays, each detector array forming a subscan assembly with one or more of the x-ray tubes, wherein the detector array and raster paths of each subscan assembly span less than 360 degrees and are located in a single plane.

34. A CT scanner for scanning an object by projecting x-ray fans from source points located along a source path to generate multiple views of the object, the CT scanner comprising:
at least two subscan assemblies defining at least two scan planes that are offset with respect to each other along a depth direction, each subscan assembly comprising approximately 5–10 rastered x-ray tubes that are located in fixed positions in the corresponding scan plane and positioned approximately in a circular arc about the object, each x-ray tube characterized by a raster path that subtends between approximately 10–30 degrees of the source path and capable of producing x-ray fans projected from different points located along the raster path, wherein substantially all of the source points along the source path of the CT scanner are located on at least one of the raster paths of the x-ray tubes;
a mechanism for moving the object relative to the subscan assemblies along the depth direction; and
a controller for activating the source points along the source path in a predetermined sequence synchronized to the relative motion of the object, wherein the synchronization compensates for the offset of the subscan assemblies along the depth direction.

35. A CT scanner for scanning an object by projecting x-ray fans from source points located along a source path to generate multiple views of the object, the CT scanner comprising:
at least two subscan assemblies defining at least two scan planes that are offset with respect to each other along a depth direction, each subscan assembly comprising approximately 5–10 rastered x-ray tubes that are located in fixed positions in the corresponding scan plane and positioned approximately in circular arc about the object, each x-ray tube characterized by a raster path that subtends between approximately 10–30 degrees of the source path and capable of producing x-ray fans projected from different points located along the raster path, wherein substantially all of the source points along the source path of CT scanner are located on at least one of the raster paths of the x-ray tubes;
a mechanism for moving the object relative to the subscan assemblies along the depth direction; and
a controller for activating the source points along the source path and for recording corresponding depths for views acquired by the subscan assemblies, wherein each x-ray tube is positioned such that the raster paths of adjacent x-ray tubes are substantially continuous.

36. A CT scanner for scanning an object by projecting x-ray fans from source points located along a source path to generate multiple views of the object, the CT scanner comprising at least two rastered x-ray tubes, each x-ray tube characterized by a raster path and capable of producing x-ray fans projected from different points along the raster path, wherein the source path of the CT scanner comprises the raster paths of the x-ray tubes, wherein each x-ray tube is positioned such that the raster paths of adjacent x-ray tubes are substantially continuous.

37. The CT scanner of claim 36 wherein at least one x-ray tube comprises:
   a target, wherein the raster path of the x-ray tube is located on the target;
   a source for generating an electron beam directed towards the target; and
   a raster mechanism for rastering the electron beam to different points along the raster path on the target.

38. The CT scanner of claim 36 wherein the x-ray tubes are movable in the scan plane in order to produce a full set of views.

39. The CT scanner of claim 36 wherein the raster path for each x-ray tube is straight.

40. The CT scanner of claim 36 wherein the raster path for each x-ray tube is curved.

41. A method for scanning an object comprising:
   providing at least two rastered x-ray tubes, each x-ray tube comprising a raster path, each x-ray tube is positioned such that the raster paths of adjacent x-ray tubes are substantially continuous;
   activating each x-ray tubes in a predetermined sequence, each x-ray tube configured to produce x-ray fans projected from different points along the raster path;
   when an x-ray tube is activated, activating source points located on the raster path for the x-ray tube in a predetermined sequence, thereby projecting x-ray fans from the sources points in the predetermined sequence, the x-ray fans producing views of the object.

42. The method of claim 41 wherein the step of activating the source points located on the raster path comprises:
   scanning an electron beam along the raster path.

43. The method of claim 41 wherein the x-ray tubes are located in fixed positions in a scan plane and substantially all of the source points along the source path are located on at least one of the raster paths.

44. The method of claim 41 further comprising the step of:
   combining the views to reconstruct images of the object.

45. A CT scanner for scanning an object comprising:
   a plurality of rastered x-ray tubes, each rastered tube comprising a raster path;
   a source path positioned around the object to be scanned;
   a detector array positioned around the object to be scanned and generally opposite the source path; and
   a controller coupled to the source path and the detector array for synchronizing activation of source points along the source path to detection by the detector array of x-ray fans projected from the source points through the object, wherein the source points are activated at a rate sufficient to produce at least 10 full sets of views per second, wherein each x-ray tube is positioned such that the raster paths of adjacent x-ray tubes are substantially continuous.

46. The CT scanner of claim 45 wherein the object to be scanned includes checked bags and the source points are activated at a rate sufficient to scan at least 1000 checked bags or break bulk items per hour.

* * * * *